United States Patent
Sanders

(10) Patent No.: US 9,963,695 B2
(45) Date of Patent: *May 8, 2018

(54) DIAGNOSIS OF PROSTATE CANCER

(71) Applicant: Quest Diagnostics Investments Incorporated, Wilmington, DE (US)

(72) Inventor: Heather R. Sanders, Winchester, CA (US)

(73) Assignee: QUEST DIAGNOSTICS INVESTMENTS INCORPORATED, Wilmington, DE (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/593,921

(22) Filed: May 12, 2017

(65) Prior Publication Data

US 2017/0342402 A1  Nov. 30, 2017

Related U.S. Application Data

(63) Continuation of application No. 13/997,868, filed as application No. PCT/US2011/067880 on Dec. 29, 2011, now Pat. No. 9,663,781.

(60) Provisional application No. 61/428,750, filed on Dec. 30, 2010.

(51) Int. Cl.
   *C12P 19/34*   (2006.01)
   *C12N 15/10*   (2006.01)
   *C12Q 1/68*    (2006.01)

(52) U.S. Cl.
   CPC ....... *C12N 15/1017* (2013.01); *C12Q 1/6806* (2013.01); *C12Q 1/6886* (2013.01); *C12Q 2600/158* (2013.01)

(58) Field of Classification Search
   USPC .................................. 435/6.11, 6.12, 91.2
   See application file for complete search history.

(56) References Cited

U.S. PATENT DOCUMENTS

| 2009/0197250 A1 | 8/2009 | Cottrell et al. |
| 2010/0196426 A1 | 8/2010 | Skog et al. |
| 2011/0111976 A1 | 5/2011 | Fare et al. |
| 2011/0159550 A1 | 6/2011 | Sanders et al. |

OTHER PUBLICATIONS

Cheruvanky et al., "Rapid isolation of urinary exomsomal biomarkers using a nanomembrane ultrafiltration concentrator," Am. J. Physiol Renal Physiol, vol. 292, pp. F1657-F1661, 2007.

Guyon et al., "A Four-Gene Expression Signature for Prostate Cancer Cells Consisting of $UAP_1$, $PDLIM_5$, $IMPDH_2$, and $HSPD_1$," UroToday International Journal, Jan. 2009, vol. 2, iss. 4, doi:10.3834/uij.1944-5784.2009,08.06, 11 pages.

International Search Report issued in application No. PCT/US2011/067880 dated Apr. 24, 2010.

Miranda et al., "Nucleic acids within urinary exomsomes/microvesicles are potential biomarkers for renal disease," Kidney International, vol. 78, pp. 191-199, 2010.

*Primary Examiner* — Kenneth R Horlick
(74) *Attorney, Agent, or Firm* — Foley & Lardner LLP

(57) ABSTRACT

The invention provides methods for isolating RNA from whole urine and urine fractions for the diagnosis of prostate cancer and/or benign prostate hyperplasia. An exemplary method for diagnosing prostate cancer in an individual, said method comprises: (a) determining the amount of RNA encoding one or more diagnostic genes in the soluble urine fraction of a urine sample obtained from said individual; (b) comparing the amount of said RNA to a reference value for said one or more diagnostic genes, wherein said reference value is derived from the amount of RNA encoding said one or more diagnostic genes in one or more individuals that do not have prostate cancer; and (c) diagnosing said individual as having prostate cancer when the amount of said RNA is greater than said reference value.

11 Claims, 5 Drawing Sheets

DIAGNOSIS OF PROSTATE CANCER

CROSS-REFERENCE TO RELATED APPLICATIONS

This application is a continuation of U.S. patent application Ser. No. 13/997,868, filed Sep. 9, 2013, now U.S. Pat. No. 9,663,781, which is a U.S. national stage of PCT/US2011/067880, filed Dec. 29, 2011, which claims priority to U.S. Provisional Application No. 61/428,750, filed on Dec. 30, 2010, incorporated by reference herein in its entirety.

FIELD OF THE INVENTION

This invention relates to methods for isolating, processing, and identifying nucleic acids from biological samples, including urine, for diagnosing prostate disease including prostate cancer.

BACKGROUND OF THE INVENTION

Prostate cancer is a cancer of the prostate gland, a small, walnut-sized structure making up a part of a man's reproductive system that wraps around the urethra. Early detection of prostate cancer, for example, prior to presentation of symptoms, can improve patient prognosis. It is estimated that there are 200,000 new cases and 25,000 deaths from prostate cancer each year in the United States. Jemal A, et al. CA Cancer J Clin. 2008; 58(2):71-96. Cancer cells with a Gleason grade 3 or 4 generally indicate aggressive cancers that require treatment. The prostate-specific antigen (PSA) test measures the amount of PSA in a blood sample of a patient and is used to determine if a patient should receive a biopsy test. However, the PSA test detects both benign prostate hyperplasia (BPH) and prostate cancer, therefore only 20-30% of biopsies are found to be positive for cancer. Out of those patients with negative results from a first biopsy, approximately 10% of second biopsies are found to be positive for cancer. Guyon, I. et al. Urotoday Int J. 2009 August; 2(4). In addition, biopsy is an invasive procedure that can result in complications such as septicemia, infections, hemorrhages, hematomas, arteriovenous fistula, tumor dissemination, bladder perforation, urinary obstruction, severe pain, strokes, perineum abscesses, erectile dysfunction, loss of desire and reduced sexual activity.

SUMMARY OF THE INVENTION

The present invention relates to methods for diagnosing prostate cancer (PCa) and/or distinguishing prostate cancer from benign prostate hyperplasia (BPH) in an individual by assessing urinary RNA levels.

In one aspect, the invention provides a method for diagnosing prostate cancer in an individual, the method comprises: (a) determining the amount of RNA encoding one or more diagnostic genes in the soluble urine fraction of a urine sample obtained from said individual; (b) comparing the amount of said RNA to a reference value for the one or more diagnostic genes, wherein the reference value is derived from the amount of RNA encoding the one or more diagnostic genes in one or more individuals that do not have prostate cancer; and (c) diagnosing the individual as having prostate cancer when the amount of said RNA is greater than the reference value.

The RNA in the soluble urine fraction may be concentrated to form a soluble urine concentrate by any suitable means including, for example, ultrafiltration (e.g., using a filter membrane having a cutoff of about 100 kDa, 50 kDa, 10 kDa, or 3 kDa), lyophilization, dialysis, or other means for dehydration or concentration. In some embodiments, the soluble urine fraction is obtained by concentrating whole urine obtained from the individual by ultrafiltration. In some embodiments, the soluble urine concentrate is formed by ultrafiltration of the soluble urine fraction through a membrane filter having a suitable molecular weight cutoff; such as a filter having a nominal molecular weight limit of not more than about 50,000 daltons; such as a filter having a nominal molecular weight limit of not more than about 3,000 daltons. In still other embodiments, the soluble urine fraction produced by the ultrafiltration is cell-free.

Ultrafiltration may be performed using a syringe filter or a centrifugal filtration unit. In some embodiments, the membrane filter has a net positive or net neutral charge. Suitable membrane materials include, for example, cellulose based materials (e.g. regenerated cellulose, methylcellulose, cellulose triacetate), polysulfone, and polyethersulfone. Dialysis may be performed against any suitable countersolvent including for, example, polyethylene glycol, and the dialysis membranes are designed to have any appropriate molecular weight cutoff, as described herein. In embodiments which use lyophilization to form the soluble urine concentrate, the urine sediment is physically separated from the soluble urine fraction prior to lyophilization. Optionally, the lyophilized product containing the RNA from the soluble fraction is resuspended (solubilized) following lyophilization in a volume of diluent less than the original volume of the urine sample.

The RNA from the soluble urine concentrate may be isolated by any suitable method including, for example, solid phase extraction. Optionally, the RNA is subsequently released from the solid phase for further processing.

In one example, the above methods further include detecting the RNA (e.g., mRNA) from the soluble urine concentrate. Exemplary methods for detecting RNA include reverse transcription coupled with real-time PCR, northern blot, UV spectroscopy, hybridization of RNA or cDNA to a probe such as in microarray or flow cytometry.

Urine may be obtained from any individual. An individual may be healthy and without any known disease. Alternatively, an individual may be a person suspected of having a disease. Urine samples may be pooled from multiple individuals or from multiple samples obtained from a single individual. In the latter case, the combined sample may represent the total daily urinary output of a single individual. Preferably, urine samples are collected in sterile containers in order to minimize the possibility for contamination by environmental microorganisms or other foreign matter. In one embodiment, the urine sample is obtained using a catheter.

In some embodiments, at least one of the diagnostic genes is heat shock 60 kDa protein 1 (HSPD1), inosine monophosphate dehydrogenase 2 (IMPDH2), PDZ and LIM domain 5 (PDLIM5), UDP-N-acteylglucosamine pyrophosphorylase 1 (UAP1), and prostate cancer antigen-3(PCA3). In some embodiments the diagnostic genes comprise each of HSPD1, IMPDH2, PDLIM5, and UAP1.

The amount of RNA encoding one or more diagnostic genes present in the soluble urine fraction is determined by reverse-transcriptase PCR (RT-PCR). For example, the determination by RT-PCR can be performed in real-time. In some embodiments, the Ct value is used to determine the amount of one or more of said diagnostic gene RNA.

Optionally, the amount of one or more of the diagnostic gene RNA is normalized to the amount of control gene RNA. The control gene RNA may be, for example, RNA encoding prostate-specific antigen (PSA), c-abl oncogene 1, receptor tyrosine kinase (ABL1), beta actin (ACTB), beta-2 microglobulin (B2M), glyceraldehyde-3-phosphate dehydrogenase (GAPDH), and beta glucuronidase (GUSB), or fragments thereof.

In some embodiments, the amount of one or more of said diagnostic genes is normalized to the amount of control gene RNA using the formula: Normalized Diagnostic Gene Score=Ln(Diagnostic Gene/Control Gene). In some embodiments, the amount of two or more diagnostic gene RNAs are determined. In certain embodiments, the amount of the diagnostic gene RNAs are used to generate a single diagnostic score, wherein the single diagnostic score is compared against a reference value for the single diagnostic score in order to diagnose said individual. In certain embodiments, the amount of each of the diagnostic gene RNAs is normalized to the amount of control gene RNA using the formula: Normalized Diagnostic Gene Score=Ln(Diagnostic Gene RNA/Control Gene RNA). In some embodiments, the single diagnostic score is calculated as the sum of the individual Normalized Diagnostic Gene Scores.

In some embodiments the control gene RNA encodes PSA or GAPDH. In some embodiments, the reference value is between about 2.6 and about 5.0; such as about 2.6 or about 5.0.

Optionally, an individual diagnosed as having prostate cancer is indicated for prostate cancer therapy. In certain embodiments, prostate cancer therapy is initiated on the individual following a positive diagnosis.

As used herein the term "diagnosing," "diagnosis," and the like means determining a disease state or condition in an individual in such a way as to inform a health care provider as to the necessity or suitability of a treatment for that individual. Optionally, an individual for which a specific diagnosis is made is further indicated for treatment for that disease state or condition. Optionally, treatment of the individual is initiated based on that diagnosis.

As used herein the term "soluble fraction of urine" means urine which is substantially free (preferably, less than about 1% w/w) of cells, cellular debris, organelles, organisms, and insoluble matter (e.g., mineral crystals). Typically, an unprocessed urine sample obtained from an individual is a mixture of the soluble fraction and the urine sediment, with the soluble fraction making up the largest portion of the mixture. Under normal conditions, the material that makes up the urine sediment is suspended in the soluble fraction and requires processing to effect useful separation. Preferably, the soluble fraction of urine and the resulting soluble urine concentrate are acellular (i.e., lacking cells). It is understood that the urine fraction may be rendered acellular (e.g., by filtration and/or centrifugation) without necessarily removing all other insoluble matter such as organelles, cellular debris, and insoluble matter.

As used herein the term "urine sediment" means that fraction of urine comprising cells, cellular debris, organelles, organisms, and/or insoluble matter that may be removed from the soluble fraction of urine. Exemplary methods for separating urine sediment from soluble fraction of urine include centrifugation, filtration, and/or sedimentation under gravity.

As used herein the term "soluble urine concentrate" means that soluble fraction of urine which is substantially free (preferably, less than about 1% w/w) of cells, cellular debris, organelles, and organisms and where the volume of the soluble fraction of urine has been reduced by at least 50%, at least 60%, at least 75%, at least 80%, at least 90% or more from the original urine volume.

As used herein the term "ultrafiltration" means a separation process which includes a filtration through a semi permeable membrane under a positive pressure such that solutes of higher molecular weight are retained by the membrane while water and low molecular weight solutes pass though the membrane. Exemplary positive pressure includes but not limited to hydrostatic pressure, centrifugal force.

As used herein the term "nominal molecular weight limit" in the context of a filter membrane means a pore size where over 90% of the solute with that molecular weight will be retained. Exemplary nominal molecular weight limit suitable for concentrating soluble urine fraction comprising RNA include 3 kDa, 10 kDa, 30 kDa, 50 kDa and 100 kDa.

The term "RNA" is meant to include mRNA, tRNA, and rRNA. In preferred embodiments, the RNA is mammalian RNA (e.g., RNA obtained from mammalian urine). In other embodiments, the RNA is non-viral.

"Primer" refers to an oligonucleotide that hybridizes to a substantially complementary target sequence and is capable of acting as a point of initiation of DNA synthesis when placed under conditions in which primer extension is initiated (e.g., primer extension associated with an application such as PCR). An oligonucleotide "primer" may occur naturally, as in a purified restriction digest or may be produced synthetically. Primers are typically between about 10 and about 100 nucleotides in length, preferably between about 15 and about 60 nucleotides in length, more preferably between about 20 and about 50 nucleotides in length, and most preferably between about 25 and about 40 nucleotides in length. An optimal length for a particular primer application may be readily determined in the manner described in H. Erlich, PCR Technology, Principles and Application for DNA Amplification (1989).

A "probe" refers to an oligonucleotide that interacts with a target nucleic acid via hybridization. A probe may be fully complementary to a target nucleic acid sequence or partially complementary. The level of complementarity will depend on many factors based, in general, on the function of the probe. A probe or probes can be used, for example to detect the presence or absence of an RNA or cDNA in a sample by virtue of the sequence characteristics of the target. Probes can be labeled or unlabeled, or modified in any of a number of ways well known in the art. A probe may specifically hybridize to a target nucleic acid. Probes can be designed which are between about 10 and about 100 nucleotides in length and hybridize to the target nucleic acid such as RNA or cDNA. Oligonucleotides probes are preferably 12 to 70 nucleotides; more preferably 15-60 nucleotides in length; and most preferably 15-25 nucleotides in length. The probe may be labeled with a detectable label.

DETAILED DESCRIPTION OF THE INVENTION

Figure 1:
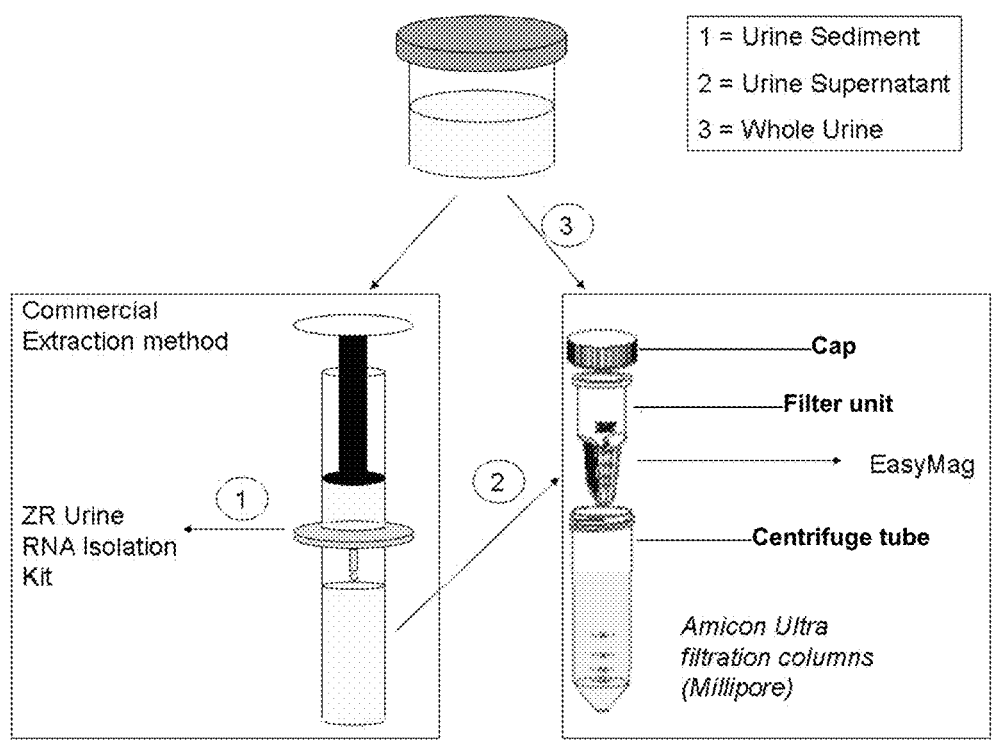
FIG. 1 shows a schematic of the experimental design of isolating RNA from urine sediment, urine filtrate (after removing cells from urine by filtration) and whole urine. Three different RNA isolation procedures are illustrated.

The present invention provides methods for diagnosing prostate cancer (PCa) and/or distinguishing prostate cancer from benign prostate hyperplasia (BPH) in an individual. The method assesses the RNA from one or more diagnostic genes in the soluble urine fraction; optionally a soluble urine concentrate. In some embodiments, the amount of diagnostic gene RNA is used to generate a diagnostic score which is compared to a reference value for that diagnostic score in order to inform the diagnosis.

Diagnostic Genes

The RNA from any gene having a known association (over-expression or under-expression) with prostate cancer may be assessed in the methods of the present invention. Without wishing to be bound by any theory, it is believed that malignant cells die and release their contents into the soluble urine fraction and/or are shed into the urine where the cells deteriorate, releasing their contents, including nucleic acids. The amount of diagnostic gene RNA may be increased in the soluble urine fraction by palpating the prostate (i.e., by a digital rectal examination) prior to urine sample collection. Some diagnostic genes suitable for analysis in the present diagnostic methods are provided below. Additional diagnostic genes are disclosed in U.S. Patent Publication 2009/0226915 and Guyon et al. (Urotoday Int. J. 2(4), 2009).

Heat Shock 60 kDa Protein-1 (HSPD1):

HSPD1 is a mitochondrial molecular chaperone which mediates protein folding in normal cells and may function as a signaling molecule in the innate immune system. In one example, the cDNA encoding human HSPD1 is provided at Genbank Accession No. $NM_{13}$ 002156.

Inosine Monophosphate Dehydrogenase-2 (IMPDH2):

IMPDH2 is the rate-limiting enzyme in the de novo guanine nucleotide biosynthesis. The enzyme is involved in maintaining cellular guanine deoxy- and ribonucleotide pools needed for DNA and RNA synthesis by catalyzing the NAD-dependent oxidation of inosine-5'-monophosphate into xanthine-5'-monophosphate, which is then converted into guanosine-5'-monophosphate. In one example, the cDNA encoding human IMPDH2 is provided at Genbank Accession No. NM_000884.

PDZ and LIM Domain-5 (PDLIM5):

PDLIM5 encodes a LIM domain protein (i.e., cysteine-rich double zinc fingers) that act as scaffolds for the formation of multiprotein complexes for cytoskeleton organization, cell lineage specification, and organ development. The encoded protein is also a member of the Enigma class of proteins, a family of proteins that possess a 100-amino acid PDZ domain in the N terminus and 1 to 3 LIM domains in the C terminus. Several PDLIM5 variants are known. The cDNA encoding some human PDLIM5 variants are provided at Genbank Accession No. NM_006457, NM_001011516, NM_001011513, and NM_001011515.

UDP-N-acetylglucosamine pyrophosphorylase-1 (UAP1):

UAP1 is also known as AgX-1 and encodes an enzyme involved in aminosugars metabolism. In one example, the cDNA encoding human UAP1 is provided at Genbank Accession No. S73498.

Control Genes

The absolute amount of RNA from any one or more diagnostic genes present in urine (or a urine fraction) may be informative of a diagnosis. However, it may be desirable to control for inter- and intra-individual differences in the amount of urinary RNA. Thus, the amount of diagnostic gene RNA may be normalized either to the total amount of RNA present in the urine sample (or urine fraction), or to the amount of RNA from a gene that is not associated with the disease state (e.g., prostate cancer). Suitable control genes may be identified by comparing the RNA levels in the urine fraction of interest from normal individuals and individuals diagnosed as having disease. Those candidate genes that have substantially the same levels between the two groups may be useful as control genes. Suitable control genes include, for example, c-abl oncogene 1 (c-abl1), receptor tyrosine kinase (ABL1), beta actin (ACTB), beta-2 microglobulin (B2M), glyceraldehyde-3-phosphate dehydrogenase (GAPDH), and beta glucuronidase (GUSB).

Prostate-specific antigen (PSA) may be used either as a control gene or as a diagnostic gene. PSA is well-known to be over-expressed and released from prostate tumors and is commonly assessed in blood, wherein elevated levels indicate prostate cancer. Thus, the amount of PSA RNA in urine also may be taken as an indicator of prostate cancer. Alternatively, the ratio of one or more diagnostic genes to PSA in urine is also informative on the diagnosis of prostate cancer. Thus, PSA may serve as the control/comparator gene in these cases.

Urine Samples

A urine sample typically consists of a soluble fraction and a sediment fraction. The sediment fraction may contain cells, cellular debris, organelles, microorganisms, and/or insoluble minerals (e.g., kidney stones). Soluble urine fraction is substantially free (less than 1% w/w) of urine sediment and preferably contains only soluble molecules (e.g., urea, nucleic acids, soluble proteins, etc.). Urine samples may be obtained from healthy individuals (i.e., free of known disease) or individuals known or suspected to have a disease or other condition. Alternatively, a urine sample may consist of urine samples pooled from several individuals.

Methods for Separating Urine Sediment from Soluble Urine Fraction

The urine sediment may be separated from the soluble urine fraction by any convenient method including, for example, centrifugation, sedimentation under gravity, or filtration. In one example, centrifugation can be performed at 1000×g to 30,000×g for 10 minutes to pellet the urine sediment and some or all of the soluble urine fraction may be removed. In another example, urine sediments can be separated by filtration using relatively high molecular weight cutoff filters such that the urine sediment is retained on the filter membrane while the soluble urine fraction including the soluble RNA passes into the filtrate. Exemplary filter membranes can be made of cellulose based membranes (e.g. regenerated cellulose, methylcellulose, cellulose triacetate), polysulfone, polyethersulfone. Commercial kits such as ZR Urine RNA Isolation Kit™ (ZYMO Research Corporation) are available to remove urine sediments from soluble urine fraction.

Methods for Concentrating Soluble Urine Fractions

Soluble urine fractions may be concentrated by any convenient method suitable for the volume of urine to be processed and the anticipated size of the soluble RNA to be identified and isolated. Suitable concentration methods include, for example, ultrafiltration, lyophilization, and dialysis (e.g., against polyethylene glycol). Ultrafiltration, involves filtration though a semi permeable membrane under a positive pressure such as hydrostatic pressure or centrifugal force such that solutes of higher molecular weight remain in the retentate while water and low molecular weight solutes pass into the filtrate. Typically, the membranes used for concentration have a smaller pore diameter (e.g., lower molecular weight cutoff) than the filters used to remove the urine sediment.

Preferably, the semipermeable membrane materials used for concentrating soluble urine fractions do not bind or retain soluble RNA. Suitable materials include, for example, cellulose based materials (e.g. regenerated cellulose, methylcellulose, cellulose triacetate), polysulfone, and polyethersulfone. The semipermeable membranes are available in various pore sizes. The pore size where over 90% of the solute with that molecular weight will be retained is termed as "nominal molecular weight limit" (NMWL). Exemplary nominal molecular weight limits suitable for isolating RNA from urine include 3 kDa, 10 kDa, 30 kDa, 50 kDa and 100 kDa. The pore size of semipermeable membranes include nominal molecular weight limits that can range from about 1 kDa to about 200 kDa, from about 2 kDa to about 150 kDa, and from about 3 kDa to about 100 kDa. Table 1 below provides general guidance for selecting the membrane for retention of RNA based on the nucleotide content of a nucleic acid. Alternatively, the soluble RNA is retained on the filter and later recovered. Suitable membranes for soluble RNA retention include anionic membranes such as PVDF.

TABLE 1

NMWL guidelines for selecting semipermeable membrane for ultrafiltration.

| NMWL | Single-stranded nucleotide cut-off (bases) | Double-stranded nucleotide cut-off (base pair) |
|---|---|---|
| 3 kDa | 10 | 10 |
| 10 kDa | 30 | 20 |
| 30 kDa | 60 | 50 |
| 50 kDa | 125 | 100 |
| 100 kDa | 300 | 125 |

Various commercially available ultrafiltration kits and devices are available to concentrating a sample such as Amicon Ultra-4 Centrifugal Filter Units, Amicon Ultra-15 Centrifugal Filter Units, Centricon® centrifugal filter devices (Millipore, Mass., USA), Pierce Concentrator (Thermo Fisher Scientific, Ill., USA). In one example, 15 ml of soluble urine fraction can be concentrated to 500 µl using Amicon Ultra-15 Centrifugal Filter Units by centrifugation for 30 minutes at 4000×g.

In one example, soluble urine fraction can be concentrated by lyophilization. Lyophilization is a freeze-drying process that works by freezing the material and then reducing the surrounding pressure and adding enough heat to allow the frozen water in the material to sublime directly from the solid phase to gas. Lyophilization machines are available from commercial vendors such as Labconco (MO, USA), Millrock Technology (NY, USA).

In another example, soluble urine fraction can be concentrated by placing the soluble urine fraction by dialysis against a solution containing polyethylene glycol and using a dialysis bag with appropriate molecular cutoff. The molecular weight cutoff can range from 3 kDa-100 kDa depending on the size of RNA to be retained within the dialysis bag. Appropriate dialysis tubings can be obtained commercially such as Sigma-Aldrich, Thermo-Scientific.

Methods for RNA Isolation and Extraction

RNA may be isolated and extracted from aqueous samples such as soluble urine fraction or soluble urine concentrate using standard techniques, see, e.g., Sambrook, et al., Molecular Cloning: A Laboratory Manual, Second Edition (1989), Cold Spring Harbor Press, Plainview, N.Y. Particularly useful are solid phase extraction methods. Reagents and kits for isolating RNA from a biological sample are commercially available e.g., RNeasy Maxi Kit, RNeasy Protect Mini kit, RNeasy Protect Cell Mini kit, QIAamp RNA Blood Mini kit, from Qiagen; MELT™, RNaqueous®, ToTALLY RNA™, RiboPure™-Blood, Poly(A)Purist™ from Applied Biosystems; TRIZOL® reagent, Dynabeads® mRNA direct kit from Invitrogen. In one example, kits provided by Qiagen employ silica resin to bind nucleic acid including RNA. RNA in the solution binds to the silica resin while the proteins and other solutes passes through. After several steps of washing, RNA can be eluted using the buffer provided by the manufacturer. In one example, NucliSENS® easyMAG® automated system (bioMérieux, Inc., NC, USA) may be used for the extraction of total nucleic acids including RNA. RNA from soluble urine fraction or soluble urine concentrate will bind to NucliSENS® magnetic silica particles. The RNA bound to the magnetic silica particles will be washed with wash buffer supplied by the manufacturer and will be eluted from the magnetic silica particles by heating using manufacturer's protocol. In another example, RNA can be isolated by adsorbing on an anion exchange resin followed by elution with high salt buffer. Exemplary anion exchange resins include Diethylaminoethyl (DEAE) crosslinked to polystyrene or cellulose, DNAPac® series of polymer-based anion-exchange columns from Dionex, anion exchange columns from Thermo Scientific.

Reverse Transcription of RNA to cDNA

Various methods to reverse transcribe RNA to cDNA are known in the art. Various reverse transcriptases may be used, including, but not limited to, MMLV RT, RNase H mutants of MMLV RT such as Superscript and Superscript II (Life Technologies, GIBCO BRL, Gaithersburg, Md.), AMV RT, and thermostable reverse transcriptase from Thermus Thermophilus. In one example, RNA extracted from soluble urine fraction or soluble urine concentrate may be reverse transcribed to cDNA using the protocol adapted from the Superscript II Preamplification system (Life Technologies, GIBCO BRL, Gaithersburg, Md., catalog no: 18089-011), as described by Rashtchian, A., PCR Methods Applic. (1994), 4:S83-S91. The method is described below.

One (1) to five (5) micrograms of RNA extracted from soluble urine fraction or soluble urine concentrate in 13 µl of DEPC-treated water is added to a clean microcentrifuge tube. One microliter of either oligo (dT) (0.5 mg/ml) or random hexamer solution (50 ng/µl) is added and mixed gently. The mixture is then heated to 70 degrees centigrade for 10 minutes and then incubated on ice for one minute. Then, it is centrifuged briefly followed by the addition of 2 µl of 10× Synthesis buffer (200 mM Tris-HCl, pH 8.4, 500 mM KCl, 25 mM magnesium chloride, 1 mg/ml of BSA), 1 µl of 10 mM each of dNTP mix, 2 µl of 0.1 M DTT, 1 µl of SuperScript IT RT (200 U/µl) (Life Technologies, GIBCO BRL, Gaithersburg, Md.). After gentle mixing, the reaction is collected by brief centrifugation, and incubated at room temperature for 10 minutes. The tube is then transferred to a 42° C. water bath or heat block and incubated for 50 minutes. The reaction is then terminated by incubating the tube at 70° C. for 15 minutes, and then placing it on ice. The reaction is collected by brief centrifugation, and 1 µl of RNase H (2 units) is added followed by incubation at 37° C. for 20 minutes before proceeding to nucleic acid amplification.

In another example, reverse transcription of RNA to cDNA was combined with the RT-PCR reaction using RNA UltraSense® one-step real-time (RT) PCR System (Invitrogen).

Detection of RNA

The presence or amount of RNA isolated from soluble urine fraction or soluble urine concentrate can be determined by several methods known in the art. In one example, RNA can be detected by Northern blot. See, e.g., Sambrook, et al., Molecular Cloning: A Laboratory Manual, Second Edition (1989), Cold Spring Harbor Press, Plainview, N.Y. In another example, RNA can be detected by reverse transcription coupled with PCR, including real-time PCR. The cDNA is amplified in a real-time PCR reaction using gene specific primers. Real-time PCR detects the copy number of PCR templates such as cDNA in a PCR reaction. Exemplary methods for quantification of RNA by real-time PCR is described by Nolan et al. (Nat Protoc. 2006; 1(3):1559-82) and Gertsch et al. (Pharm Res. 2002 August; 19(8):1236-43). The references are incorporated herein by reference. In another example, RT-PCR is performed in a combination with a reverse transcription of RNA to cDNA reaction using RNA UltraSense® one-step real-time (RT) PCR System (Invitrogen).

In one example, amplification of cDNA is monitored by SYBR green dye. The dye binds to double-stranded (ds) DNA in PCR, causing fluorescence of the dye. An increase in DNA product during PCR therefore leads to an increase in fluorescence intensity and is measured at each cycle, thus allowing DNA concentrations to be quantified.

In another example, amplification of cDNA is monitored by TaqMan® probes (Heid et al., Genome Res. 1996; 6: 986-994). TaqMan® probes are based on the principle of fluorescence quenching and involve a donor fluorophore and a quenching moiety. The term "fluorophore" as used herein refers to a molecule that absorbs light at a particular wavelength (excitation frequency) and subsequently emits light of a longer wavelength (emission frequency). The term "donor fluorophore" as used herein means a fluorophore that, when in close proximity to a quencher moiety, donates or transfers emission energy to the quencher. As a result of donating energy to the quencher moiety, the donor fluorophore will itself emit less light at a particular emission frequency than it would have in the absence of a closely positioned quencher moiety.

The term "quencher moiety" as used herein means a molecule that, in close proximity to a donor fluorophore, takes up emission energy generated by the donor and either dissipates the energy as heat or emits light of a longer wavelength than the emission wavelength of the donor. Suitable quenchers are selected based on the fluorescence spectrum of the particular fluorophore. Useful quenchers include, for example, the Black Hole™ quenchers BHQ-1, BHQ-2, and BHQ-3 (Biosearch Technologies, Inc.), TAMRA, 4-(4-dimethylaminophenylazo) benzoic acid (DABCYL), and the ATTO-series of quenchers (ATTO 540Q, ATTO 580Q, and ATTO 612Q; Atto-Tec GmbH). TaqMan® probes are designed to anneal to an internal region of a PCR product. When the polymerase (e.g., reverse transcriptase) replicates a template on which a TaqMan® probe is bound, its 5' exonuclease activity cleaves the probe. This ends the activity of the quencher (no FRET) and the donor fluorophore starts to emit fluorescence which increases in each cycle proportional to the rate of probe cleavage. Accumulation of PCR product is detected by monitoring the increase in fluorescence of the reporter dye. If the quencher is an acceptor fluorophore, then accumulation of PCR product can be detected by monitoring the decrease in fluorescence of the acceptor fluorophore.

To ensure accuracy in the quantification, it is usually necessary to normalize expression of a target gene to one or more reference genes that are stably expressed. Exemplary reference genes include beta actin (ACTB), beta-2 micro globulin (B2M), glyceraldehyde-3-phosphate dehydrogenase (GAPDH). Relative concentrations of DNA present during the exponential phase of the reaction are determined by plotting fluorescence against cycle number on a logarithmic scale (so an exponentially increasing quantity will give a straight line). A threshold for detection of fluorescence above background is determined. The cycle at which the fluorescence from a sample crosses the threshold is called the cycle threshold, Ct. A lower Ct value indicates higher copy number of an RNA. Amounts of RNA is determined by comparing the results to a standard curve produced by real-time PCR of serial dilutions of a known amount of RNA or DNA.

Detection by Hybridization.

RNA isolated from soluble urine fraction or soluble urine concentrate can be detected following reverse transcription and amplification by hybridization with a nucleic probe that hybridizes specifically to the RNA of interest (i.e., a target RNA). The methods of the present invention can incorporate all known methods and means and variations thereof for carrying out DNA hybridization, see, e.g., Sambrook, et al., 1989, Molecular Cloning: A Laboratory Manual, Second Edition, Cold Spring Harbor Press, Plainview, N.Y.

The RNA or cDNA may form a complex on a solid support prior to being detected. The complex may comprise a capture probe anchored to a solid support, the RNA of interest hybridized to the capture probe, and a detectably labeled probe hybridized to the RNA of interest. In some cases, the solid support may comprise a first member of a binding pair and the capture probe may comprise a second member of the binding pair. The binding of the first member of the binding pair to the second member of the binding pair may anchor the capture probe to the solid support. Examples of solid support include but are not limited to beads, microparticles, microarray plates, microwells. Examples of binding pair include but are not limited to biotin/streptavidin, ligand-receptor, hormone-receptor, and antigen-antibody.

RNA and/or cDNA can be detected by performing an array-based hybridization to detect the genes of interest in a sample, or to diagnose a disease in an individual. The resolution of array-based method is primarily dependent upon the number, size and map positions of the nucleic acid elements within the array, which are capable of hybridizing to the RNA. Microarrays are available commercially that cover all human genes. For example, GeneChip® Human Exon 1.0 ST Array from Affymetrix (CA, USA), Whole Human Genome Microarray Kit from Agilent Technologies (CA, USA) are capable of evaluating gene expression of all known transcripts in human.

Alternatively, the hybridized complexes can also be detected using flow cytometry. Flow cytometry is a technique well-known in the art. Flow cytometers hydrodynamically focus a liquid suspension of particles (e.g., cells or synthetic microparticles or beads) into an essentially single-file stream of particles such that each particle can be analyzed individually. Flow cytometers are capable of measuring forward and side light scattering which correlates with the size of the particle. Thus, particles of differing sizes may be used in invention methods simultaneously to detect distinct nucleic acid segments. In addition fluorescence at one or more wavelengths can be measured simultaneously. Consequently, particles can be sorted by size and the fluorescence of one or more fluorescent labels probes can be analyzed for each particle. Exemplary flow cytometers include the Becton-Dickenson Immunocytometry Systems FACSCAN. Equivalent flow cytometers can also be used in the invention methods.

Example 1

Detection of RNA from Large Volume of Liquid Sample

The ability to detect RNA in a large volume of liquid sample was tested by adding 5 µl of RNA (845.6 ng/µl) to 15 ml of Tris-EDTA (TE) buffer. The resulting RNA solution was concentrated to less than 500 µl by centrifugation using Amicon Ultra-15 filter units with nominal molecular weight limit of 3 kDa and 10 kDa (Millipore, Mass., USA). The concentration of RNA in the retentate from two different membrane filters were determined using NanoDrop™ spectrophotometer (Thermo Scientific), which requires small volume of sample for analysis. The recovery of RNA were comparable from the two membrane filter types: 94% for 10 kDa and 100% for 3 kDa. The results are shown in Table 3 below.

TABLE 2

Retention of spiked cell line RNA in TE measured by Nanodrop concentration.

| Sample | Volume (µl) | Conc. (ng/µl) | Total (ng) | % Recovery |
|---|---|---|---|---|
| Spiked RNA/15 ml TE | 5 | 845.6 | 4228 | |
| 10 kDa membrane retentate | 160 | 24.9 | 3984 | 94% |
| 3 kDa membrane retentate | 270 | 15.7 | 4239 | 100% |

Example 2

Comparison of Recovery of Spiked RNA from Membranes with Different Pore Sizes

The range of filter pore sizes that can be used to concentrate the RNA were evaluated for RNA retention using filter columns ranging from 3 kDa-100 kDa. A known amount of cell line RNA (34 µg) was spiked into a large volume of TE buffer (75 ml), split into five aliquots for a starting amount of 6.8 µg of total RNA per 15 ml aliquot. Each 15 ml aliquot was concentrated through five separate filter columns with different pore sizes (nominal molecular weight limit: 3 kDa, 10 kDa, 30 kDa, 50 kDa and 100 kDa retention, respectively). After concentration with the filter columns, the % recovery was determined. First, RNA yield was calculated by multiplying the final volume of sample by the final concentration of the sample measured by nanodrop. Second, the RNA yield was divided by the starting amount of RNA (6.8 µg) to give the final % recovery of each filter column. Based on these results, the 3 kDa pore size gave the highest recovery of 94%, followed by 10 kDa (87%), 30 kDa (78%), 50 kDa (80%), and 100 kDa with the lowest and final yield (67%). The results are shown in Table 3 below.

TABLE 3

Retention of spiked cell line RNA in TE measured by Nanodrop concentration.

| Sample | Volume (µl) | Conc. (ng/µl) | Total (ng) | % Recovery |
|---|---|---|---|---|
| Spiked RNA/15 ml TE | 5 | 1360 | 6800 | |
| 100 kDa membrane retentate | 135 | 33.7 | 4550 | 67% |
| 50 kDa membrane retentate | 206 | 26.4 | 5438 | 80% |
| 30 kDa membrane retentate | 290 | 18.4 | 5336 | 78% |
| 10 kDa membrane retentate | 190 | 31.3 | 5947 | 87% |
| 3 kDa membrane retentate | 428 | 15.0 | 6420 | 94% |

Example 3

Comparison of Recovery of Endogenous Urine RNA from Membranes with Different Pore Sizes Some factors may effect the efficiencies in retention of RNA in a real sample with endogenous RNA versus a sample spiked with RNA. These factors include the presence of partially degraded or fragmented RNA and the presence of urine RNases that may degrade RNA prior to processing. The ability of membranes with different pore sizes to retain endogenous urine RNA was evaluated. Whole urine (75 ml) was obtained from five separate donors and split into five 15 ml aliquots per donor. Each of the five aliquots per donor was concentrated using the filters of five different pore sizes (nominal molecular weight limit: 3 kDa, 10 kDa, 30 kDa, 50 kDa, and 100 kDa). RNA from each sample of concentrated urine was extracted using EasyMag. Amplification of two different transcripts (GAPDH and ABL1) was performed for each sample by RT-PCR. In order to quantitate retention efficiencies, RNA concentrated from the top performing filter column in the RNA spiking studies (3 kDa) was used as the baseline (100%) for each donor. Using the cycle threshold (Ct) obtained by qRT-PCR, the recoveries for the 10 kDa-100 kDa filter columns were calculated based on the 3 kDa Ct values that were set at 100%. Based on these results, retention of endogenous RNA was dependent on both the donor and the transcript, with all pore sizes above 3 kDa demonstrating significantly reduced efficiency. The average retention for pore sizes 10 kDa-100 kDa for transcript 1 ranged from 32%-47% and 16%-31% for transcript 2. The results are shown in Table 4 below.

TABLE 4

Recovery of endogenous urine RNA using filter column membranes with different pore sizes.

| Donor | Transcript 1 | | | | | Transcript 2 | | | | |
| --- | --- | --- | --- | --- | --- | --- | --- | --- | --- | --- |
| | 3 kDa | 10 kDa | 30 kDa | 50 kDa | 100 kDa | 3 kDa | 10 kDa | 30 kDa | 50 kDa | 100 kDa |
| 1 | 100% | 66% | 59% | 79% | 43% | 100% | 25% | 39% | 36% | 9% |
| 2 | 100% | 67% | 69% | 79% | 59% | 100% | 47% | 40% | 50% | 19% |
| 3 | 100% | 40% | 43% | 24% | 25% | 100% | 28% | 28% | 9% | 12% |
| 4 | 100% | 26% | 20% | 10% | 4% | 100% | 26% | 25% | 12% | 8% |
| 5 | 100% | 38% | 24% | 34% | 28% | 100% | 27% | 11% | 13% | 31% |
| Avg | 100% | 47% | 43% | 45% | 32% | 100% | 31% | 29% | 24% | 16% |

Example 4

Sample Preparation and RNA Extraction from Urine Samples

Urine sample (30 ml) was obtained from an individual with benign prostate hyperplasia was split into two 15 ml aliquots for extraction of RNA from cellular components of urine sediment and soluble urine fractions.

The first aliquot of urine was processed for RNA extraction from the cells in the urine sediment using ZR Urine RNA Isolation Kit™ (ZYMO Research Corporation). Briefly, cells were separated from urine by a syringe filter. The cells were retained on the syringe filter and the filtrate was collected separately. The retained cells were lysed directly on the filter using 700 μl of RNA Extraction Buffer Plus™ reagent (ZYMO Research Corporation) and the cell lysate was collected in a 1.5 ml tube. The cell lysate was mixed with an equal volume of ethanol and passed through Zima-Spin IC™ column. The column was washed with 300 μl of RNA Wash Buffer. Total RNA was eluted from the column by applying 25 μl of the supplied RNA Elution Buffer directly to the column membrane followed by centrifugation.

The filtrate collected from the syringe filtration step described above was further concentrated using Amicon Ultra-15, nominal molecular weight limit of 3 kDa (Millipore, Mass., USA) to a final filtrate volume of 500 μl (soluble urine concentrate), representing approximately a 30-fold concentration. The total nucleic acid was extracted from the soluble urine concentrate using NucliSENS® easyMAG® (bioMérieux, Inc., NC, USA) using manufacturer's protocol. Briefly, total nucleic acid binds to NucliSENS® magnetic silica particles. The magnetic silica particles were separated from the liquid portion using a magnetic field. The nucleic acid bound to silica particles were washed with the wash buffer provided by the manufacturer. The nucleic acid is finally released from the solid phase with the elution buffer. FIG. 1 (pathways 1 and 2) shows a schematic of the experimental design used to process the first urine aliquot (ultrafiltration step not shown).

The second urine aliquot (15 ml) was directly applied to an Amicon Ultra-15, having a nominal molecular weight limit of 3 kDa (Millipore, Mass., USA). The urine sample was concentrated to 500 μl. The total nucleic was extracted from the soluble urine concentrate using NucliSENS® easyMAG® (bioMérieux, Inc., NC, USA) using manufacturer's protocol as discussed above. FIG. 1 (pathway 3) shows a schematic of the experimental design used to process the second urine aliquot (ultrafiltration step not shown).

Example 5 cDNA Synthesis and RT-PCR cDNA Synthesis and RT-PCR were performed in a one-step process using RNA UltraSense® one-step real-time (RT) PCR System (Invitrogen): First, RNA was treated with DNase to eliminate DNA using RNA-free (Ambion). A master mix was prepared with following components for each reaction: RNA UltraSense Enzyme Mix 2.5 μl RNA UltraSense 5× Reaction Mix 10 μl, Taqman probe primer pair (10 μM concentration each) 1 μl, Fluorogenic probe (10 μM) 1 μl, ROX Reference Dye 1 μl. Next, 3 μl of RNA template in 31.5 μl of DEPC-treated water per reaction was added to a clean microcentrifuge tube. The 34.5 μl of template was added to the 15.5 μl of Master mix for a total of 50 μl for each reaction. After gentle mixing, the reaction mixture was subjected to brief centrifugation, and was placed in a preheated programmed thermal cycler. The instrument was programmed to perform cDNA synthesis immediately followed by PCR amplification using the following cycling parameters: 50° C. for 15 minute hold, 95° C. for 2 minute hold, 40-50 cycles of: 95° C. for 15 seconds and 60° C. for 30 seconds. After cycling, the reaction was held at 4° C. until further analysis.

Example 6

Estimation of Gene Expression Levels

Expression levels of four genes: heat shock 60 kDa protein 1 (HSPD1), inosine monophosphate dehydrogenase 2 (IMPDH2), PDZ and LIM domain 5 (PDLIM5), and UDP-N-acetylglucosamine pyrophosphorylase 1 (UAP1); and five reference genes: c-abl oncogene 1, receptor tyrosine kinase (ABL1), beta actin (ACTB), beta-2 microglobulin (B2M), glyceraldehyde-3-phosphate dehydrogenase (GAPDH), and beta glucuronidase (GUSB) were evaluated using the RNA UltraSense® one-step RT-PCR System. Taqman® probes were used to monitor DNA synthesis. Fluorescent signals were measured and plotted against the number of PCR cycles. The Ct value, the point at which the fluorescence crosses the baseline threshold is measured for each gene. A lower Ct value indicates higher initial concentration of template DNA and therefore initial RNA. The Ct values for four test genes and five reference genes were determined using the RNA isolated from cells present in urine, the urine supernatant which is free of cells, and whole urine without further separation of cells. The Ct values of different genes in various samples are presented in Table 5 below.

TABLE 5

Ct values of the Genes in Different Samples

| Kit | Sample | Test Genes | | | | 5 Reference Genes | | | | |
|---|---|---|---|---|---|---|---|---|---|---|
| | | HSPD1 | IMPDH2 | PDLIM5 | UAP1 | ABL1 | ACTB | B2M | GAPDH | GUSB |
| Zymo | Urine Sediment | 29.9 | 26.7 | 31.0 | 33.3 | 32.6 | 24.6 | 25.1 | 23.1 | 30.8 |
| Amicon | Urine Supernatant | 26.0 | 26.8 | 28.3 | 31.9 | 30.7 | 23.9 | 26.5 | 22.1 | 28.8 |
| | Soluble Urine Concentrate from Whole Urine (3K) | 26.6 | 24.8 | 27.1 | 30.9 | 29.8 | 21.4 | 23.0 | 20.6 | 27.3 |
| | Soluble Urine Concentrate from Whole Urine (10K) | 29.2 | 28.2 | 30.5 | 32.8 | 33.2 | 24.6 | 27.0 | 24.4 | 30.3 |

The results in Table 5 demonstrate that the amount of RNA in whole urine is generally higher than that obtained from the cells present in urine. Additionally, the urine supernatant contains more transcript than the cells in urine sediment for the majority of the genes tested. Furthermore, the expression pattern of the five reference genes varied among the cells in urine sediment, urine supernatant (after separation of cells) and soluble urine concentrate (without separation of cells). As seen in Table 5, concentration of whole urine to form a soluble urine concentrate consistently yielded higher amounts of RNA when a membrane with smaller pore size was used (cf. MW=3K versus MW=10K cutoff).

Example 7

Assessment of Diagnostic RNA for Prostate Cancer in Urine Fractions

Urine Collection and Processing:

Urine samples were collected from male individuals diagnosed as having prostate cancer prior to a prostate biopsy. Urine samples were collected from the study participants using standard urine collection cups. Each urine sample was split in order to obtain fractions of whole urine, urine sediment, and urine supernatant from each study individual. Urine supernatant was produced by filtering 15 ml of whole urine using an Amicon Ultra-15, nominal molecular weight limit of 3 kDa (Millipore, Mass., USA). Whole urine and urine sediment was processed as described above. RNA from all urine fractions was isolated using the ZR Urine RNA Isolation Kit™ (ZYMO Research Corporation) and subsequently processed, concentrated, and processed as described above. DNA was removed from the resulting nucleic acids using the DNA-free kit (Ambion, Cat. # AM1906) according to the manufacturer's protocol.

RT-PCR Amplification of Urinary RNA:

RNA from each urine fraction was quantified for the amount of prostate-specific antigen (PSA), HSPD1, UAP1, IMPDH2, and PDLIM5, and GAPDH as a control gene, by RT-PCR. The specific primers and probes are provided in Table 6. IMPDH2 and PDLIM5 were assessed using a TaqMan® Gene Expression Assay according to the manufacturer's protocols (Applied Biosystems; Cat. Nos. Hs01021353_m1 and Hs00935062_m1, respectively). qRT-PCR assays were run on an ABI 7900HT instrument with the following thermocycling conditions: Step 1: 50° C., 20 min.; Step 2: 94° C., 2 min.; Step 3: 94° C., 15 sec.; Step 4: 58-60° C., 30 sec.; cycle steps 3-4 forty five times.

TABLE 6

RT-PCR Primers/Probes For Prostate Cancer-specific Genes

| Primer/Probe | Sequence | SEQ ID NO: |
|---|---|---|
| GAPDH-F | 5'-GAA GGT GAA GGT CGG AGT C-3' | 1 |
| GAPDH-R | 5'-GAA GAT GGT GAT GGG ATT TC-3' | 2 |
| GAPDH-Probe | 5'-FAM-CAA GCT TCC CGT TCT CAG CC-BHQ-3' | 3 |
| HSPD1-F | 5'-AAC CTG TGA CCA CCC CTG AA-3' | 4 |
| HSPD1-R | 5'-TCT TTG TCT CCG TTT GCA GAA A-3' | 5 |
| HSPD1-Probe | 5'-VIC-ATT GCA CAG GTT GCT AC-BHQ-3' | 6 |
| UAP1-F | 5'-TTG CAT TCA GAA AGG AGC AGA CT-3' | 7 |
| UAP1-R | 5'-CAA CTG GTT CTG TAG GGT TCG TTT-3' | 8 |
| UAP1-Probe | 5'-VIC-TGG AGC AAA GGT GGT AGA-BHQ-3' | 9 |

Quantitation of Urinary RNA:

The amount of HSPD1, IMPDH2, PDLIM5, and UAP1 were normalized to either the concentration of GAPDH RNA or PSA RNA. A seven-point standard curve for PSA was generated using PSA concentrations of 0.0122-50.0 ng/μl. Normalized diagnostic gene scores were calculated according to the following formula:

$$\text{Normalized Diagnostic Gene Score} = \text{Ln}(\text{Diagnostic Gene RNA/Control Gene RNA})$$

wherein the Diagnostic Genes are HSPD1, IMPDH2, PDLIM5, and UAP1, individually, and the Control Gene is either GAPDH or PSA. A combined 4-gene score was calculated by summing the four Normalized Diagnostic Gene scores for each of the GAPDH and the PSA normalizations.

Figure 2:
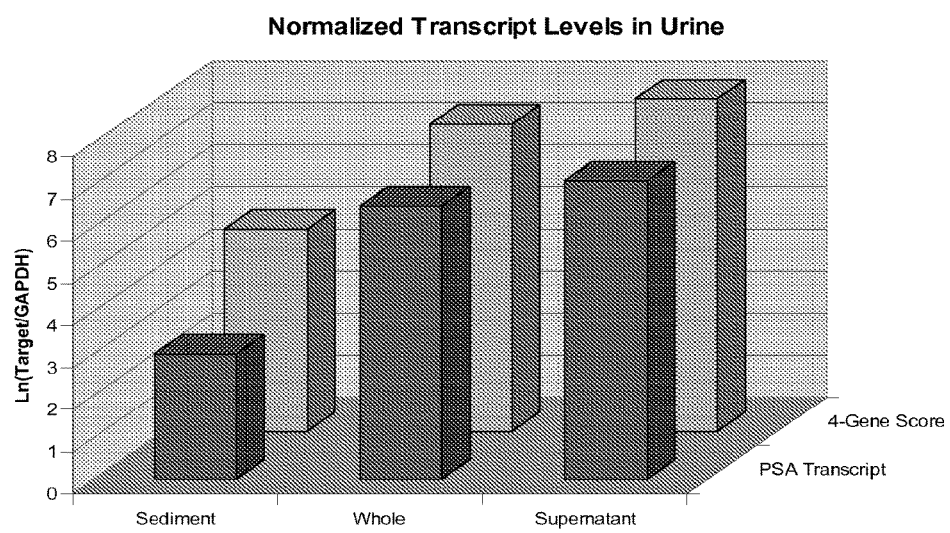
FIG. 2 is a bar graph showing the relative amount of PSA RNA recovered from various urine fractions and the diagnostic score calculated from the GADPH-normalized levels of four genes associated with prostate cancer. Experimental details are provided in Example 7.

Results:

The results of this study are illustrated in FIG. 2. Levels of PSA transcript were found to be highest in the soluble urine fraction (supernatant). Additionally, the amount of individual diagnostic gene transcripts and the diagnostic 4-gene score was also found to be highest in the soluble urine fraction indicating that this fraction provides the greatest diagnostic sensitivity and represents a significant improvement over the transcript levels detected in the urine sediment.

Example 8

Assessment of Diagnostic RNA for Prostate Cancer in Urine Fractions

Urine Collection and Processing:

Blood and urine samples were collected from male individuals diagnosed as having prostate cancer prior to a prostate biopsy, diagnosed as having benign prostate hyperplasia (BPH), or identified as not having either prostate cancer or BPH. Prostate cancer patients were males having a positive diagnosis, ages 50-75, and within 30 days of a scheduled prostate biopsy. Exclusion criteria from the patient population included a history of prior prostate cancer treatment or a previous diagnosis of any other cancer within the last five years (excluding non-melanoma skin cancer). The control populations were males, 50-75 years of age, and having a PSA result within the six months prior to sample collection of ≥1.0 ng/mL. Exclusion criteria from the control population included any prior diagnosis and/or treatment for prostate cancer or any other cancer, excluding non-melanoma skin cancer. Control subjects had to otherwise feel healthy and have no evidence of fever. Urine samples from all individuals was collected and processed as described in Example 7.

Figure 3:
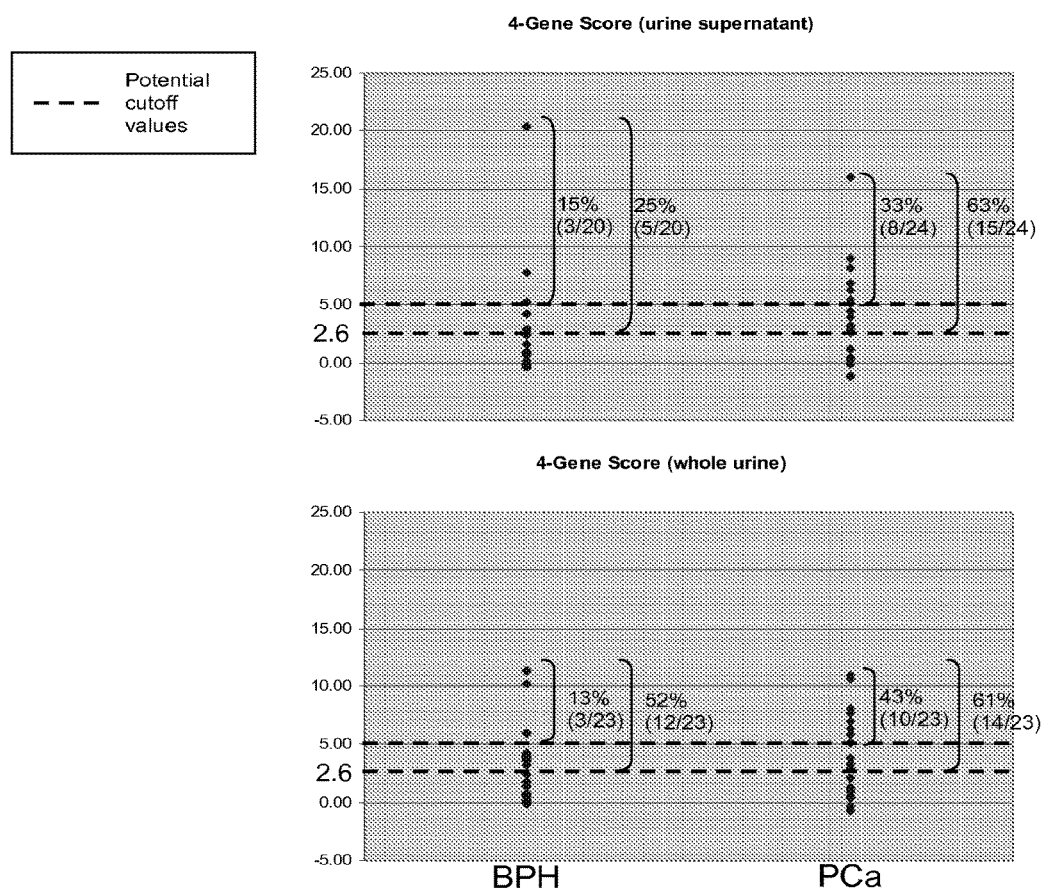
FIG. 3 is a series of graphs showing the 4-gene score of HSPD1, UAP2, IMPDH2, and PDLIM5, normalized to GAPDH, in urine supernatant (top) and whole urine (bottom) samples obtained from male patients diagnosed as having BPH or PCa. Each bar graph indicates the proportion of individuals, for each condition, having 4-gene scores above diagnostic cut-off threshold values of 2.6 and 5.0.

Four-Gene Score:

The diagnostic genes HSPD1, UAP1, IMPDH2, and PDLIM5, along with PSA were amplified and quantified from whole urine and urine supernatant (soluble urine fraction) of prostate cancer (PCa) and BPH patient samples, and the 4-gene score was calculated. All methods and calculations were performed as described in Example 7. The 4-gene score results from individual samples are provided in FIG. 3.

The diagnostic potential of various cut-off scores was investigated. Applying a diagnostic cut-off score of 2.6 to the data set in FIG. 3 resulted in the correct identification of 63% of PCa patients, while only 25% of BPH patients showed an elevated 4-gene score in the urine supernatant. A cut-off score of 5.0 resulted in the correct identification of 33% of PCa patients while only 15% of BPH patients had 4-gene scores greater than this level. When these cutoff levels were applied to the 4-gene scores determined in whole urine, the 2.6 level correctly identified 61% of PCa patients while 52% of BPH patients showed an elevated score. The 5.0 cutoff level resulted in 43% of PCa samples being correctly identified, whereas only 13% of BPH samples were elevated.

Figure 4:
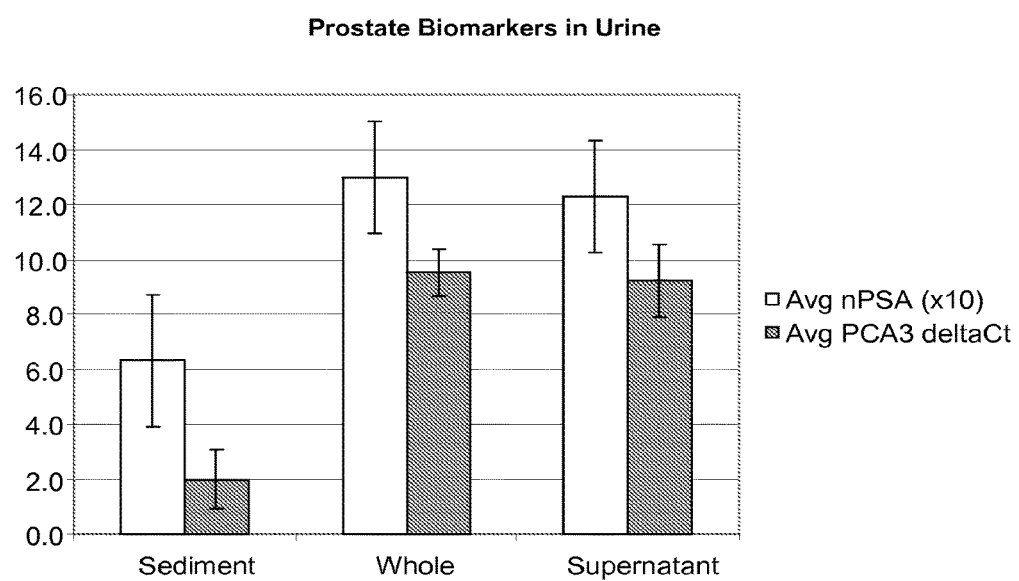
FIG. 4 is a bar graph showing the relative amount of PSA (multiplied by a factor of ten and normalized to GAPDH) and PCA3 measured in whole urine, urine sediment, and urine supernatant obtained from male patients diagnosed as have PCa. Error bars represent S.E.M.

PSA and PCA3 Levels in Whole Urine and Urine Fractions:

The relative amounts of other prostate cancer markers, PSA and PCA3, were investigated in the three urine fractions. In each fraction, the amount of PSA transcript was quantified by RT-PCR, as above, and normalized to GAPDH, as above. For convenience, the PSA level was multiplied by a factor of ten before GAPDH normalization. As shown in FIG. 4, normalized PSA levels (nPSA) were highest in whole urine and urine supernatant, which were significantly greater than nPSA levels in the urine sediment.

The Ct value for the PCA3 transcript, measured during the RT-PCR reaction was used as a relative index of the PCA3 transcript concentration present in the sample. The Ct value, in a quantitative PCR such as that used here, is the amplification cycle at which the detected fluorescence crosses a pre-determined threshold value. Thus, lower Ct values are indicative of higher starting concentrations of target nucleic acid because fewer cycles of amplification are required to reach the threshold. For convenience, the PCA3 data presented in FIG. 4 is the $45\text{-Ct}_{observed}$ in the PCA3 assay. This transformation illustrates graphically increasing values proportional to increasing starting PCA3 concentrations (FIG. 4). As was the case for nPSA, PCA3 RNA levels were highest in whole urine and urine supernatant, each of which was significantly higher than the levels measured in the urine sediment.

Figure 5:
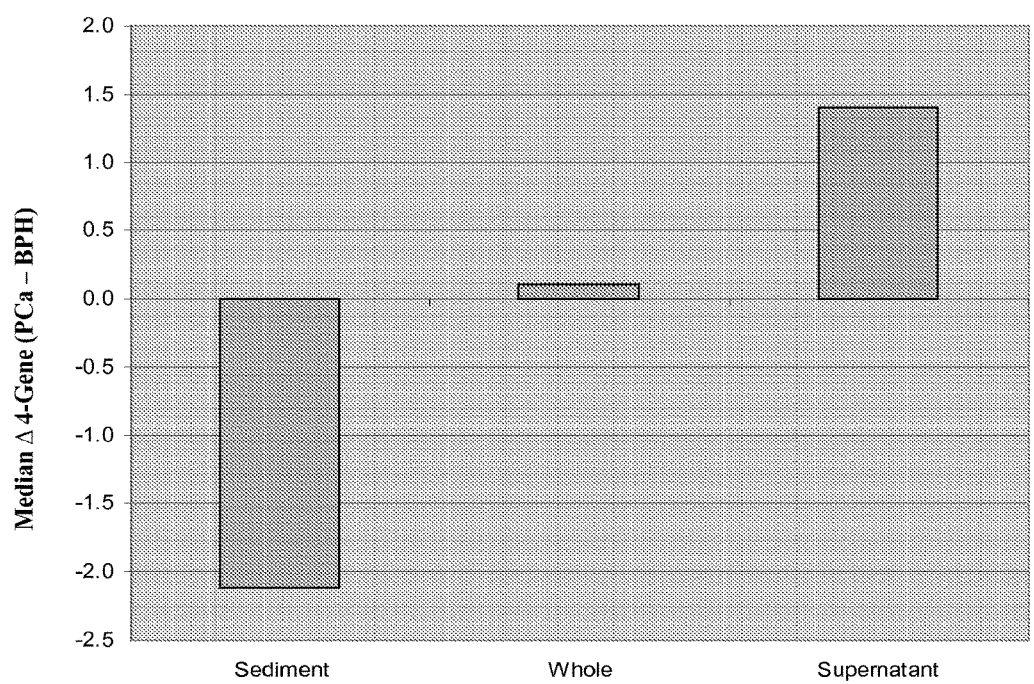
FIG. 5 is a bar graph showing the median difference in the 4-gene score normalized to PSA RNA levels in the three urine fractions between samples obtained from BPH and PCa patients.

Validation of the Soluble Urine Fraction for PCa Diagnosis:

In order to determine the relative diagnostic capacity of the soluble versus insoluble urine fractions, and whole urine, for PCa diagnosis, the 4-gene score for each patient was determined using PSA normalization according to the formulas provided in Example 7. The median 4-gene score was determined for each fraction and each disease state (PCa and BPH). For each urinary fraction, the 4-gene score for BPH was subtracted from the 4-gene score for PCa. The median differences are illustrated graphically in FIG. 5. As shown for whole urine, the median 4-gene score for PCa and BPH were approximately the same, indicating that whole urine is generally not suitable for differential PCa diagnosis using the present methods. Differences in the median 4-gene score using urine sediment samples indicate that BPH generally results in higher scores than PCa which has the potential to result in a high level of false positive PCa diagnoses. In contrast, the median 4-gene score determined in urine supernatant was greater for the PCa samples than for the BPH samples indicating that the urine supernatant has a greater capacity to be used for differential diagnosis of prostate disease.

Example 9

Clinical Study of Six-Gene Assay for Detecting Prostate Cancer

Urine was collected from 125 male subjects. The group included 50 prostate cancer (PCa) patients with urine collected before and after prostatectomy (cohort 1), 25 healthy men with serum PSA values below 1.0 ng/ml deemed unlikely to harbor prostate cancer (cohort 2), and 50 men with serum PSA values greater than 2.5 ng/ml who were scheduled for prostate biopsy (cohort 3). A subgroup of 25 men from cohort 3 had urine samples collected before and after digital rectal exam (DRE) (cohorts 4 and 5 respectively) but before biopsy. Serum from each patient was also collected and analyzed for PSA.

Urine from each subject was aliquoted into 30 mL fractions, with one fraction each for assaying supernatant, sediment, and whole urine, as well as aliquots sent to an outside laboratory to test for PCA-3. Extraction of RNA for the supernatant, sediment, and whole urine fractions was completed immediately, as described in Example 7. Each patient fraction was analyzed for the amount of four target genes and two reference genes using RT-PCR, as described in Example 5. The target genes were PDLIM5, UAP1, HSPD1, IMPDH2, and the reference genes were PSA and GAPDH. Assay results were blinded and data was correlated with the clinical findings after all assays were completed.

Example 10

Data Analysis of Urine from Clinical Study

Data from a subset of urine supernatant samples collected before DRE, as described in Example 9, were analyzed for the ability to detect prostate cancer. The supernatant samples used in the study had PSA mRNA >0.001 ng and a combined 4-target gene plus PSA mRNA >0.1 ng. The study size of 40 patients (15 PCa and 25 benign) was powered to detect an area under the receiver operating characteristic curve (AUROC) of 0.70 with ≥58% accuracy. The resulting AUROC was 0.544 (p-value=0.685). The AUROC values for the entire 4-gene panel as well as each of the individual genes in urine supernatant, urine sediment, and whole urine are summarized in Table 7 below.

TABLE 7

Pre-DRE AUROC Values to Distinguish PCa from Non-PCa

| Gene Target/Ref. | AUC (Sensitivity/Specificity) | | |
|---|---|---|---|
| Gene | Supernatant | Sediment | Whole |
| 4-gene/PSA | 0.544 (33%/68%) | 0.527 (50%/55%) | 0.516 (36%/72%) |
| HSPD1/PSA | 0.564 (60%/60%) | 0.530 (33%/77%) | 0.505 (43%/76%) |
| IMPDH2/PSA | 0.573 (47%/60%) | 0.538 (58%/50%) | 0.552 (50%/60%) |
| PDLIM5/PSA | 0.508 (40%/72%) | 0.610 (58%/68%) | 0.513 (43%/56%) |
| UAP1/PSA | 0.500 (53%/52%) | 0.506 (50%/55%) | 0.510 (50%/60%) |
| 4-gene/GAPDH | 0.552 (60%/64%) | 0.558 (55%/68%) | 0.605 (86%/52%) |
| HSPD1/GAPDH | 0.573 (67%/56%) | 0.550 (55%/59%) | 0.594 (57%/63%) |
| IMPDH2/GAPDH | 0.609 (67%/56%) | 0.574 (45%/67%) | 0.618 (86%/57%) |
| PDLIM5/GAPDH | 0.523 (47%/64%) | 0.608 (45%/58%) | 0.575 (64%/46%) |
| UAP1/GAPDH | 0.560 (60%/60%) | 0.525 (55%/59%) | 0.568 (71%/50%) |

Urine from post-DRE samples were also analyzed, with sample numbers of 23, 20, and 19 for supernatant, sediment, and whole urine, respectively. Most AUROC values were not significantly above 0.50 except for IMPDH2/PSA in urine sediment, which had an AUROC value of 0.766. Table 8 below summarizes AUROC data for urine collected after DRE.

TABLE 7

Post-DRE AUROC Values to Distinguish PCa from Non-PCa

| Gene Target/Ref. | AUC (Sensitivity/Specificity) | | |
|---|---|---|---|
| Gene | Supernatant | Sediment | Whole |
| 4-gene/PSA | 0.571 (44%/57%) | 0.688 (75%/58%) | 0.583 (57%/42%) |
| HSPD1/PSA | 0.595 (33%/71%) | 0.625 (63%/58%) | 0.607 (43%/50%) |
| IMPDH2/PSA | 0.540 (56%/50%) | 0.766 (75%/67%) | 0.530 (71%/42%) |
| PDLIM5/PSA | 0.587 (33%/43%) | 0.609 (50%/67%) | 0.607 (43%/58%) |
| UAP1/PSA | 0.595 (56%/36%) | 0.641 (63%/58%) | 0.595 (43%/42%) |
| 4-gene/GAPDH | 0.650 (67%/71%) | 0.563 (50%/75%) | 0.583 (57%/50%) |
| HSPD1/GAPDH | 0.670 (78%/71%) | 0.583 (50%/75%) | 0.589 (43%/83%) |
| IMPDH2/GAPDH | 0.686 (67%/79%) | 0.615 (50%/75%) | 0.667 (43%/100%) |
| PDLIM5/GAPDH | 0.664 (78%/64%) | 0.583 (50%/75%) | 0.613 (29%/100%) |
| UAP1/GAPDH | 0.664 (78%/57%) | 0.563 (50%/75%) | 0.637 (57%/75%) |

In the same sample subset, the PCA3 assay yielded an AUROC of 0.711. Using a PCA3 cutoff value of 35, the specificity and sensitivity for PCA3 detection were 60% and 75%, respectively.

Example 11

Data Analysis of Urine Supernatant and Urine Sediment from Clinical Study

Data from the study described in Example 9 was re-analyzed, focusing on the quality control parameters for RNA concentration. The analysis described in Example 10 included samples with PSA mRNA >0.001 ng and a combined 4-target gene plus PSA mRNA >0.1 ng. For all subjects who provided one urine sample, an average of 28% of the sediments were excluded, as were 15% of the supernatants and 17% of the whole urines. However, a review of the post-prostatectomy urine samples showed that 28 of the 49 post prostatectomy urines met the criteria of a quality sample having an adequate PSA RNA concentration, when in fact the PSA RNA values for these urines should have been zero. The PSA copy number was less than the detectable value of 3000 copies per mL in all of the post-prostatectomy sample types, confirming the absence of detectable RNA. Thus, the criteria for defining a quality sample for urine supernatant was set too low, allowing background noise to be accepted as an actual value.

In the post-prostatectomy urine supernatant samples, the highest value observed for PSA mRNA was 0.068. Thus a new criteria of 0.07 ng was selected to redefine these urine samples as not detectable for PSA RNA. The criteria of 0.001 ng for urine sediment was maintained for judging the acceptability of urine sediments for assay, as all of the post-prostatectomy urine sediments had undetectable PSA RNA.

Using these sample selection criteria for urine supernatant and sediment RNA, a subset of 46 supernatant and sediment samples were selected. An S score (sum of target gene expression normalized by the two reference genes) for this subset of samples was calculated from a linear SVM equation using the six gene expression inputs for each urine supernatant and sediment. The linear SVM is a form of the normalization equation that was published for the tissue gene test and which was used in the analysis of the data as described in Example 10. The S score was calculated for the supernatant and for its matching sediment for all urines with a supernatant PSA RNA greater than 0.07 ng. A positive classification of cancer was defined as either the supernatant or sediment being positive. A negative classification of cancer required both the supernatant and sediment to have a negative S score.

The classification achieved with the S score gave a sensitivity of 80% and specificity of 83%. An ROC curve was constructed to demonstrate the average performance over the range of S cut-off values and had an area under the curve of 0.813.

Matching data for PCA3 detection at a cutoff value of 35 gave a sensitivity of 55% and a specificity of 88%. In the entire study group of 125 subjects, in which 43 subjects were excluded due to low copy number for either PCA3 or PSA, the PCA3 detection sensitivity of the remaining subgroup was 58% with a specificity of 74%.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A detection method comprising:
   (a) separating urine sediment from a soluble urine fraction of a urine sample obtained from an individual suspected of having prostate cancer;
   (b) concentrating the soluble urine fraction by ultrafiltration to produce a soluble urine concentrate, wherein the volume of soluble urine concentrate is reduced at least 50% from the original urine volume;
   (c) detecting the amount of RNA from each of heat shock 60 kDa protein 1 (HSPD1), inosine monophosphate dehydrogenase 2 (IMPDH2), PDZ and LIM domain 5 (PDLIM5), and UDP-N-acetylglucosamine pyrophosphorylase 1 (UAP1) in the concentrated soluble urine fraction.

2. The method of claim 1, wherein the ultrafiltration comprises filtration using a filter having a nominal molecular weight limit of not more than about 50,000 daltons.

3. The method of claim 1, wherein the ultrafiltration comprises filtration using a filter having an nominal molecular weight limit of not more than about 3,000 daltons.

4. The method of claim 1, wherein the soluble urine fraction produced by the ultrafiltration is cell-free.

5. The method of claim 1, further comprising isolating the RNA from the soluble urine concentrate by solid phase extraction.

6. The method of claim 1, wherein the amount of each said RNA present in the soluble urine fraction is determined by reverse-transcriptase PCR (RT-PCR).

7. The method of claim 6, wherein the determination by RT-PCR is performed in real-time.

8. The method of claim 6, wherein the Ct value is used to determine the amount of each said RNA.

9. The method of claim 1, wherein the amount of RNA is normalized to the amount of a control gene RNA.

10. The method of claim 9, wherein the control gene RNA encodes a gene selected from the group consisting of prostate-specific antigen (PSA), c-abl oncogene 1, receptor tyrosine kinase (ABL1), beta actin (ACTB), beta-2 microglobulin (B2M), glyceraldehyde-3-phosphate dehydrogenase (GAPDH), and beta glucuronidase (GUSB).

11. The method of claim 1, further comprising detecting the amount of RNA encoding prostate cancer antigen-3 (PCA3) in the concentrated soluble urine fraction.

* * * * *

SEQUENCE LISTING

```
<160> NUMBER OF SEQ ID NOS: 9

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaaggtgaag gtcggagtc                                                19

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gaagatggtg atgggatttc                                               20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
caagcttccc gttctcagcc                                               20
```

```
<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aacctgtgac caccectgaa                                                20

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tctttgtctc cgtttgcaga aa                                             22

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
attgcacagg ttgctac                                                   17

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttgcattcag aaaggagcag act                                            23

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
caactggttc tgtagggttc gttt                                           24

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
tggagcaaag gtggtaga                                                  18
```